(12) United States Patent
Yunn-Bor et al.

(10) Patent No.: US 6,699,699 B2
(45) Date of Patent: Mar. 2, 2004

(54) MUTATED PENICILLIN EXPANDASES

(75) Inventors: Yang Yunn-Bor, Taipei (TW); Wei Chia-Li, Taipei (TW); Hsu Jyh-Shing, Taipei (TW); Tsai Ying-Chieh, Taipei (TW)

(73) Assignee: Synmax Biochemical Co., Ltd., Taipei (TW)

( * ) Notice: Subject to any disclaimer, the term of this patent is extended or adjusted under 35 U.S.C. 154(b) by 0 days.

(21) Appl. No.: 10/105,319

(22) Filed: Mar. 26, 2002

(65) Prior Publication Data
US 2003/0190695 A1 Oct. 9, 2003

(51) Int. Cl.⁷ .............................. C12P 35/00; C12N 9/10
(52) U.S. Cl. .......................................... 435/193; 435/47
(58) Field of Search .................................... 435/47, 193

(56) References Cited

U.S. PATENT DOCUMENTS

| 5,559,005 A | 9/1996 | Conder et al. |
| 5,731,165 A | 3/1998 | Bovenberg et al. |
| 5,919,680 A | 7/1999 | Sutherland et al. |

FOREIGN PATENT DOCUMENTS

| EP | 0 341 891 A1 | 11/1989 | |
| EP | 0 366 354 A2 | 5/1990 | |
| EP | 0 366 354 A3 | 5/1990 | |
| EP | 0 453 047 A1 | 10/1991 | |
| WO | WO 01/85951 | * 11/2001 | ........... C12N/15/53 |

OTHER PUBLICATIONS

Chin et al., *Biochemical and Biophysical Research Communications* 287: 507–513 (2001).
Coque J. et al., *Mol Gen Genet*. 1993;326(2–3):453–8.
Wei C.L. et al., *Appl Environ Microbiol*. 2003;69(4):2306–12.
Wong E. et al., *Biochem Biophys Res Commun*. 2001;283(3):621–6.

* cited by examiner

Primary Examiner—Rebecca E. Prouty
Assistant Examiner—Sheridan L. Swope
(74) Attorney, Agent, or Firm—Pennie & Edmonds LLP

(57) ABSTRACT

A mutated expandase enzyme having higher activity on penicillin G is provided to produce phenylacetyl-7-aminodeacetoxycephalosporanic acid (7-ADCA), which mutated expandase enzyme has one or more amino acid substitutions selected from M73T, G79E, V275I, L277K, C281Y, G300V, N304K, I305L and I305M.

6 Claims, 4 Drawing Sheets

SEQUENCE LISTING

<160> NUMBER OF SEQ ID NOS: 1

<210> SEQ ID NO 1
<211> LENGTH: 1230
<212> TYPE: DNA
<213> ORGANISM: Streptomyces clavuligerus
<220> FEATURE:
<221> NAME/KEY: CDS
<222> LOCATION: (232)...(1164)

<400> SEQUENCE: 1

```
cccgggtgcc gctggtcagc gccaccggat cgacccgtat gggccgcgcc gtgggccccc      60
gggccggtgc tccggatctc ggcgaacttc tacaccaccg aagaggagat cgaccgcctg     120
gcggacgcgc tggacgcgct gacgggcgag tgatcccccc ggctcgcgga ccgcctcccc     180
cgcgctgttg accacccggt tcacggatta cgagaggatc agtgagagtt g atg gac      237
                                                         Met Asp
                                                           1 acg acg gtg ccc acc ttc agc ctg gcc gaa ctc cag cag ggc ctg cac        285
Thr Thr Val Pro Thr Phe Ser Leu Ala Glu Leu Gln Gln Gly Leu His
        5                  10                  15 cag gac gag ttc cgc agg tgt ctg agg gac aag ggc ctc ttc tat ctg        333
Gln Asp Glu Phe Arg Arg Cys Leu Arg Asp Lys Gly Leu Phe Tyr Leu
 20                  25                  30 acg gac tgc ggt ctg acc gac acc gag ctg aag tcg gcc aag gac atc        381
Thr Asp Cys Gly Leu Thr Asp Thr Glu Leu Lys Ser Ala Lys Asp Ile
 35                  40                  45                  50 gtc atc gac ttc ttc gag cac ggc agc gag gcg gag aag cgc gcc gtc        429
Val Ile Asp Phe Phe Glu His Gly Ser Glu Ala Glu Lys Arg Ala Val
                 55                  60                  65 acc tcg ccc gtc ccc acc atg cgc cgc ggc ttc acc ggg ctg gag tcg        477
Thr Ser Pro Val Pro Thr Met Arg Arg Gly Phe Thr Gly Leu Glu Ser
             70                  75                  80 gag agc acc gcc cag atc acc aat acc ggc agc tac tcc gac tac tcg        525
Glu Ser Thr Ala Gln Ile Thr Asn Thr Gly Ser Tyr Ser Asp Tyr Ser
         85                  90                  95 atg tgc tac tcg atg ggc acc gcg gac aac ctc ttc ccg tcc ggt gac        573
Met Cys Tyr Ser Met Gly Thr Ala Asp Asn Leu Phe Pro Ser Gly Asp
    100                 105                 110 ttc gag cgg atc tgg acc cag tac ttc gac cgc cag tac acc gcc tcc        621
Phe Glu Arg Ile Trp Thr Gln Tyr Phe Asp Arg Gln Tyr Thr Ala Ser
115                 120                 125                 130
```

-continued

```
cgc gcg gtc gcc cgg gag gtc ctg cgg gcg acc ggg acc gag ccc gac    669
Arg Ala Val Ala Arg Glu Val Leu Arg Ala Thr Gly Thr Glu Pro Asp
            135             140             145 ggc ggg gtc gag gcc ttc ctc gac tgc gag ccg ctg ctg cgg ttc cgc    717
Gly Gly Val Glu Ala Phe Leu Asp Cys Glu Pro Leu Leu Arg Phe Arg
            150             155             160 tac ttc ccg cag gtc ccc gag cac cgc agc gcc gag gag cag ccc ctg    765
Tyr Phe Pro Gln Val Pro Glu His Arg Ser Ala Glu Glu Gln Pro Leu
            165             170             175 cgg atg gcg ccg cac tac gac ctg tcg atg gtc acc ctc atc cag cag    813
Arg Met Ala Pro His Tyr Asp Leu Ser Met Val Thr Leu Ile Gln Gln
        180             185             190 aca ccc tgc gcc aac ggc ttc gtc agc ctc cag gcc gag gtc ggc ggc    861
Thr Pro Cys Ala Asn Gly Phe Val Ser Leu Gln Ala Glu Val Gly Gly
195             200             205             210 gcg ttc acg gac ctg ccc tac cgt ccg gac gcc gtc ctc gtc ttc tgc    909
Ala Phe Thr Asp Leu Pro Tyr Arg Pro Asp Ala Val Leu Val Phe Cys
                215             220             225 ggc gcc atc gcg acc ctg gtg acc ggc ggc cag gtc aag gcc ccc cgg    957
Gly Ala Ile Ala Thr Leu Val Thr Gly Gly Gln Val Lys Ala Pro Arg
            230             235             240 cac cat gtc gcg gcc ccc cgc agg gac cag ata gcg ggc agc agc cgc   1005
His His Val Ala Ala Pro Arg Arg Asp Gln Ile Ala Gly Ser Ser Arg
        245             250             255 acc tcc agt gtg ttc ttc ctc cgt ccc aac gcg gac ttc acc ttc tcc   1053
Thr Ser Ser Val Phe Phe Leu Arg Pro Asn Ala Asp Phe Thr Phe Ser
    260             265             270 gtc ccg ctg gcg cgc gag tgc ggc ttc gat gtc agc ctg gac ggc gag   1101
Val Pro Leu Ala Arg Glu Cys Gly Phe Asp Val Ser Leu Asp Gly Glu
275             280             285             290 acc gcc acg ttc cag gat tgg atc ggg ggc aac tac gtg aac atc cgc   1149
Thr Ala Thr Phe Gln Asp Trp Ile Gly Gly Asn Tyr Val Asn Ile Arg
                295             300             305 cgc aca tcc aag gca tagagagcac acaccgtcat ggtcacagca gcaatcagtg   1204
Arg Thr Ser Lys Ala
            310 gtaccgacga gatacgcgcg agggcg                                       1230
```

US 6,699,699 B2

MUTATED PENICILLIN EXPANDASES

FIELD OF THE INVENTION

The present invention relates to a mutated penicillin expandase having high substrate specificity to penicillin G, recombinant cells expressing the mutated expandase, and a process of preparing 7-aminodeacetoxycephalosporanic acid (7-ADCA) using the mutated expandase.

BACKGROUND OF THE INVENTION 7-aminodeacetoxycephalosporanic acid (7-ADCA) is one of the important intermediates for the production of cephalosporins cefalexin, cefradine, and cefadroxil which are antibiotic compounds commonly and long used in humans and animals. The industrial process to synthesize 7-ADCA mainly includes two steps: a chemical ring expansion of penicillin G to phenylacetyl-7-ADCA and an enzymatic side chain cleavage of phenylacetyl-7-ADCA. However, the chemical reaction of the ring expansion is complex and expensive, and the by-products and the organic solvents (such as pyridine and HBr) are toxic to the environment. Therefore, an enzymatic reaction is greatly desirable to replace such chemical reaction.

It has been reported that a natural enzyme, deacetoxycephalosporain C synthase (DAOCS, or expandase), may be responsible for the catalysis of the expansion reaction. Streptomyces sp. (such as *Streptomyces clavuligerus, Streptomyces ambofaciens* and *Streptomyces chartreusis*) can produce the expandase. As illustrated in EP-A-034 1892, the expandase can be obtained from *Streptomyces clavuligerus*, and has been cloned. The expandase has been well studied for its chemical and functional properties, see EP-A-0366354. Unfortunately, the native expandase has less substrate specificity to penicillin G than the normal substrate penicillin N (Rollins, M. J. et al., *Can. J Microbiol.* 34: 1196–1202 (1988) and Crawford, L. et al., *Bio/Technology*, 13: 58–62 (1995)) Penicillin G is commercially available at a low cost. In contrast, penicillin N is expensive and not easily available. Furthermore, even though penicillin N is expanded, its side chain cannot be easily removed. Accordingly, the chemical synthesis of 7-ADCA, rather than an enzymatical synthesis, is still used in industrial production.

There are a number of applications directed to producing 7-ADCA by expandase. U.S. Pat. No. 5,731,165 describes a process for the preparation and recovery of 7-ADCA via enzymatic ring expansion activity on penicillin G, using a *Penicillium chrysogenum* transformant strain expressing expandase. U.S. Pat. No. 5,559,005 discloses a bioprocess for preparing 7-amino-cephalosporanic acid (7-ACA) or 7-ADCA using a transformed stain of *Penicillium chrysogenum* having expandase activity capable of accepting adipoyl-6-amino-penicillanic acid (adipoyl-6-APA) as a substrate. Nevertheless, since both adipoyl-6-APA and penicillin G are poor substrates for native expandase in vitro (U.S. Pat. No. 5,559,005), it is not optimistic to have a high expansion efficiency while applied in vivo.

Recently, Chih H. S. et al. (*Biochemical and Biophysical Research Communications*, 287: 507–513 (2001)) discloses a mutated DAOCS comprising an amino acid substitution of N304L. U.S. Pat. No. 5,919,680 describes a mutated expandase which has an altered amino acid sequence from a native expandase, resulting in an altered substrate specificity. Several amino acid positions have been mentioned in that patent, and the mutated expandase created by changing one or more of the mentioned amino acids shows a higher activity ratio of penicillin G to penicillin N in a mixture of these two substrates, but has a lower activity on penicillin G and penicillin N individually than wild-type expandase. Therefore, there is still a need to develop a mutated penicillin expandase having more substrate specificity and enzymatic activity on penicillin G.

SUMMARY OF THE INVENTION

The present invention provides mutated expandase having expansion activities 2 to 32 folds higher on penicillin G than wild-type expandase.

One object of the invention is to provide a mutated penicillin expandase which comprises an amino acid substitution at one or more residue positions corresponding to those of a wild-type expandase selected from the group consisting of methionine 73, glycine 79, valine 275, leucine 277, cysteine 281, glycine 300, asparagine 304 and isoleucine 305, provided that the amino acid substitution at the residue position of asparagine 304 is not N304L. In particular, the invention provides a mutated penicillin expandase which comprises one or more specific amino acid substitutions selected from the group consisting of M73T, G79E, V275I, L277K, C281Y, G300V, N304K, I305L and I305M, wherein the residue positions of the amino acid substitution correspond to those of a wild-type expandase.

Another object of the invention is to provide an isolated nucleic acid molecule encoding the mutated penicillin expandase.

Another object of the invention is to provide a recombinant vector comprising the nucleic acid molecule of the invention and a regulatory sequence operatively linked thereto.

Still another object of the invention is to provide recombinant cells comprising the nucleic acid molecule of the invention.

In another aspect, the invention provides a method to produce a mutated penicillin expandase. In one embodiment of the invention, the method comprises expressing the nucleic acid molecule of the invention and recovering the mutated penicillin expandase. In another embodiment of the invention, the method comprises culturing the recombinant cells of the invention to express the mutated penicillin expandase and recovering the mutated penicillin expandase form the cell culture.

In another aspect, the invention provides a process for producing 7-ADCA comprising treating penicillin G with the mutated penicillin expandase of the invention to produce phenylacetyl-7-ADCA, followed by deacylating the phenylacetyl-7-ADCA to produce the 7-ADCA.

In still another aspect, the invention provides a process for producing 7-ADCA, which process comprises the steps of (a) cultivating penicillin G producing cells which is transformed with the nucleic acid molecule of the invention under conditions suitable for production of penicillin G and expression of the mutated penicillin expandase such that the penicillin G is expanded by the mutated expandase and phenylacetyl-7-ADCA is produced; (b) deacylating the phenylacetyl-7-ADCA to produce the 7-ADCA.

The present invention will be fully understood from the detailed description and figures as given below.

DETAILED DESCRIPTION OF THE INVENTION

Figure 1:
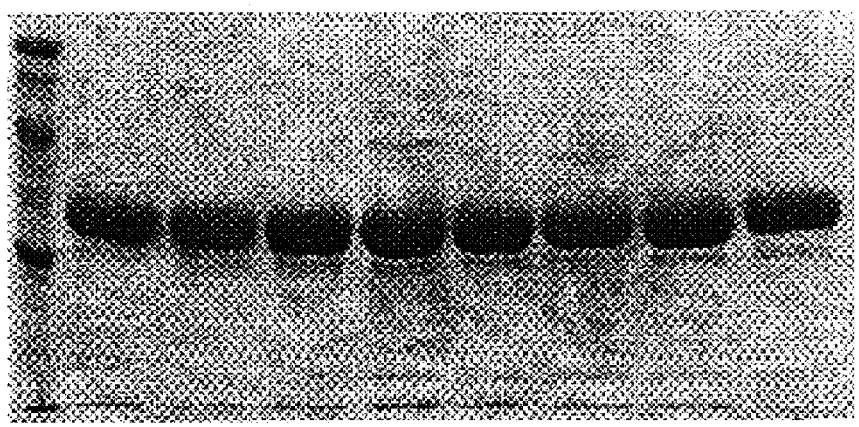
FIG. 1 shows the SDS-PAGE results of the purified DAOCS of the invention. Lanes 1 to 9 represent molecular weight markers and the purified DAOCS of YS5, YS8, YS11, YS12, YS16, YS49, YS53 and YS59 mutants, respectively. Each loaded DAOCS dose was in an amount of 5 μg.

The primary aspect of the present invention is to provide a mutated penicillin expandase having a better substrate specificity to penicillin G, wherein the mutated penicillin expandase comprises an amino acid substitution at one or more residual positions corresponding to those of a wild-type expandase selected from the group consisting of methionine 73, glycine 79, valine 275, leucine 277, cysteine 281, glycine 300, asparagine 304 and isoleucine 305, provided that the amino acid substitution at the residue position of asparagine 304 is not N304L. More specifically, the invention provides a mutated penicillin expandase comprising one or more specific amino acid substitutions selected from the group consisting of M73T, G79E, V275I, L277K, C281Y, G300V, N304K, I305L and I305M.

A "wild type penicillin expandase", as used herein, refers to the native penicillin expandase obtained from Streptomyces sp. Preferably, the wild-type expandase is obtained from *Streptomyces clavuligerus*. The native penicillin expandase and its corresponding gene (cefE gene) have been well characterized and described in the prior art (e.g., EP-A-0366354 and EP-A-0341892). Persons skilled in the art can readily obtain the nucleic acid sequences of the wild-type penicillin expandase and the corresponding amino acid sequences from the prior art.

The mutated penicillin expandase of the invention comprises the functional equivalents of the same. As used herein, the "functional equivalents" of the mutated penicillin expandase may contain further amino acid mutations (e.g., deletions, additions or substitutions) located at positions other than those described above, wherein said further amino acid mutations result in silent changes and thus do not substantially affect the function (e.g., enzyme activity) of the mutated penicillin expandase. Furthermore, in the "functional equivalents" of the mutated penicillin expandase, the specific amino acid substitutions (i.e., selected from M73T, G79E, V275I, L277K, C281Y, G300V, N304K, I305L and I305M) may be exchanged with other amino acid substitutions of similar characteristics which result in a silent change. For example, a mutated penicillin expandase with an amino acid substitution of "G79D" is functional equivalent to that with an amino acid substitution of "G79E", since the amino acid D (aspartic acid) and B (glutamic acid) are both classified as acid amino acids and are of similar characteristics.

In another aspect, the invention provides an isolated nucleic acid molecule encoding the mutated penicillin expandase of the invention. The isolated nucleic acid molecule of the invention is obtained by mutating the nucleic acid encoding the wild-type penicillin expandase. A conventional mutation-inducing technical is well known in the art, such as irradiation of with gamma rays or ultraviolet light or treatment with a mutagen, such as hydroxylamine and ethylmethane, or site-directed mutagenesis. Persons skilled in the art can choose a suitable mutagenesis technology to obtain a mutated nucleic acid molecule. The mutated nucleic acid molecules can be further cloned and selected for their biological activities. More detailed technologies, comprising mutagenesis, cloning and screening for biological activities, used to obtain the isolated nucleic acid molecules of the invention are described in the following examples.

According to the invention, the isolated nucleic acid may be inserted into a vector to form a recombinant vector. The term "vector" used herein means a nucleic acid molecule, which is capable of carrying and transferring a nucleic acid segment of interest into a host cell for the purpose of expression or replication of the same. In particular, a vector refers to a plasmid, cosmid, bacteriophage or virus. Typically, the nucleic acid segment of interest is operatively linked to a regulatory sequence such that, when introducing into a host cell, for instance, the nucleic acid segment can be expressed in the host cell under the control of the regulatory sequence. The regulatory sequence may comprise, for example, a promoter sequence (e.g., cytomegalovirus (CMV) promoter, simian virus 40 (SV40) early promoter and T7 promoter), replication origin and other control sequences (e.g., Shine-Dalgano sequences and termination sequences). Preferably, the nucleic acid segment of interest may be connected to another nucleic acid fragment such that a fused polypeptide (e.g., His-tag fused polypeptide) is produced and beneficial to the subsequent purification procedures. The method for identifying and selecting the regulatory sequences are well known to the skilled persons and widely described in the literatures. The skilled persons can readily construct the recombinant vector of the invention according to the specification and the well-known technologies.

The recombinant vector of the invention can be introduced into host cells to produce the mutated penicillin expandase. Accordingly, recombinant cells transformed with the recombinant vector is within the scope of the invention. Such recombinant cells can be prokaryotic (e.g., bacteria) or eukaryotic (e.g., fungi, animal and plant cells). In particular, the recombinant cells of the invention are penicillin G producing cells, preferably *Penicillium chrysogenum* cells, which can be used to produce 7-ADCA in vivo, as described below. A number of transformation technologies, such as a calcium chloride treatment, Calcium-PEG procedure, electroporation, DEAE-dextrin-mediated transfection, lipofection and microinjection are well described in many literatures. The skilled persons can choose a proper technology depending on the nature of the host cells and the vector to be introduced in the host cells.

A method for producing the mutated penicillin expandase is also provided in the invention. The recombinant cells described above can be cultured in a suitable condition to express the mutated penicillin expandase and then the expressed expandase is recovered and purified. Those skilled in this art will appreciate that the recovering and purifying method is widely described in many references and is not limited, for example, by various chromatographies (e.g., HPLC or affinity columns).

The genetic engineering methods mentioned above such as DNA mutagenesis, cloning, vector construction, transformation, protein expression, and purification can be accomplished by those skilled in this art, and which can be seen, for example, in Molecular Cloning: A Laboratory Manual, 2d ed., Cold Spring Harbor Laboratory Press, Sambrook, J., E. F. Fritsch and T. Maniatis eds. (1989).

The present invention is also related to a process to produce 7-ADCA, which process comprises the steps of treating penicillin G with the mutated penicillin expandase of the invention to produce phenylacetyl-7-ADCA and deacylating the phenylacetyl-7-ADCA to produce the 7-ADCA. In particular, the mutated expandase is expressed and recovered as stated above, and then added with the substrate penicillin G. The mixture is incubated under conditions (e.g., at a temperature of 30° C.) suitable for the enzyme activity of the mutated expandase such that a ring expansion reaction is conducted by the mutated expandase and the substrate penicillin G is converted to phenylacetyl-7-ADCA. Preferably, phenylacetyl-7-ADCA is purified through a simple solvent extraction, for example, and then treated with a suitable enzyme (e.g., penicillin amidase, as described in EP-A-0453047) such that the phenylacetyl side chain is removed and the desired 7-ADCA is obtained. In another aspect, the substrate penicillin G can be directly added into the cell culture of the recombinant cells expressing the mutated expandase of the invention. The expressed expandase then reacts with the penicillin G and converts it into phenylacetyl-7-ADCA, followed by deacylation of the phenylacetyl-7-ADCA to produce the desired 7-ADCA.

It has been found that penicillin G producing cells (e.g., *Penicillium chrysogenum*) transformed with an expandase-encoding gene is capable of producing phenylacetyl-7-ADCA in vivo. Accordingly, another aspect of the invention is to provide a process to produce 7-ADCA using penicillin G producing cells, which process comprises the steps of (a) cultivating penicillin G producing cells which is transformed with the recombinant vector of the invention under conditions suitable for production of penicillin G and expression of the mutated expandase of the invention such that the penicillin G is expanded by the mutated expandase and phenylacetyl-7-ADCA is produced; (b) deacylating the phenylacetyl-7-ADCA to produce the 7-ADCA. The term "penicillin G producing cells" used herein refers to cells capable of naturally producing penicillin G in a normal condition without any genetic engineering technologies (e.g., transformation). Preferably, the penicillin G producing cells are cells of *Penicillium chrysogenum*. The phenylacetyl-7-ADCA produced from Step (a) can be optionally purified by filtration and extraction steps. The detailed procedures, such as transformation and fermentation of such cells and purification of the produced phenylacetyl-7-ADCA, have been described in the prior art, such as U.S. Pat. No. 5,919,680 and EP 5,731,165 which are incorporated herein for reference.

EXAMPLES

The present invention will become apparent with reference to the examples below. The examples described below are given by way of illustration only and are not intended to be any limitation of the present invention.

Materials

All chemicals were purchased from Merck unless stated otherwise. Strain *Streptomyces clavuligerus* was ordered from Culture Collection & Research Center (Taiwan). Oligonucleotides were synthesized by Genset (Singapore Biotech). DNA sequences were analyzed by Mission Biotech (Taiwan). Liquid chromatography- Mass analysis was performed by Protech Laboratory (Taiwan). Penicillin G was from Harbin Pharmaceutical Co. (China). $C^{14}$-penicillin G was ordered from Moravek. Penicillin N, deacetoxycephalosporin C, and cephalosporin G were synthesized in this laboratory. Other materials and supplied companies are indicated as follow: enzymes for DNA manipulation (Promega); Zero Blunt TOPO PCR cloning kit (Invitrogen); DNA gel extraction kit, GFX Micro Plasmid Prep kit, & FPLC apparatus and columns (Amersham Pharmacia Biotech Inc.); PCR clean up-M (Viogene); pET24a, pET30a, BL21(DE3), and Tuner cells (Novagen); Bradford reagent, 30% acrylamide/bis-acrylamide solution, and PAGE apparatus (Bio-Rad); HPLC set (LC-10AT, Sil-10AD, SPD-10A; Shimadzu); $C_{18}$ column (250×4.6 mm, 5$\mu$; Hypersil); HPLC data analysis software (Scientific Information Service Corporation); pefabloc SC, and leupeptin (Roche)

Example 1

Random Mutagenesis

The cefE gene fragment was cut off from pYB4, a pET24a backbone with a BamHI-Hind III cefE insert cloned from *Streptomyces clavuligerus* using Zero Blunt TOPO PCR Cloning kit, treated with 0.8 M hydroxylamine at 65° C. for 2 hours, cleaned up with PCR Clean up-M kit, then ligated back into the backbone vector. This mutated cefE pool was transformed into BL21(DE3) by electroporation, and transformants were selected on LB plates with 50 $\mu$g/ml of kanamycin. The mutated transformants were subjected for an activity improvement screening.

Example 2

Activity Improvement Screening

The mutated transformants were grown in a 96-well plate containing 56.7 $\mu$l of LB medium with kanamycin in each well. Then 0.1 mM IPTG was added into each well to induce DAOCS indirectly at 30° C. for 2 hours of shaking, followed by another 1 hour of shaking after an addition of 7 $\mu$l of 100 mg/ml lysozyme. The activity of DAOCS was measured by an addition of 30 $\mu$l of assay mixture (500 mM Mops/pH 7.0, 18 mM FeSO$_4$, 40 mM ascorbate, 25.6 mM $\alpha$-ketoglutarate and suitable amount of penicillin G), and incubated at 30° C. for another 1 hour of shaking. The resulting mixture was loaded on an 8 mm thick paper disc, and placed onto a bioassay plate seeded with *Eseherichia coli* ESS strain (a $\beta$-lactum supersensitive mutant, a gift from Dr. Demain) as described in Cho H. et al., *Proc. Natl. Acad Sci. USA*, 95: 11544–11548 (1988). The transformants with clear zone bigger than that of unmutated control strain were selected and subjected for further activity confirmation by TLC. After the activity improvement screening, the mutated cefE was manipulated into a NdeI-Hind III insertion version in the same vector (pET24a), and the mutants such as YS5 (V275I), YS53 (C281Y) and YS59 (G79E) were selected.

A TLC method to separate penicillin G and cephalosporin G was also developed for bioassay screening. Silica plates 60 F254 were used as a solid phase and the mobile phase was a mixture of chloroform: acetone: acetic acid=6:5:0.5 (volume ratio). $C^{14}$ labeled penicillin G was used in the standard assay with 20 $\mu$g of cell extract (quantitated with Bio-Rad Bradford kit using BSA as a standard), and after addition of ethanol the mixture was applied directly onto TLC plate without centrifugation.

Example 3

Site-Directed Mutagenesis

The wild-type expandase gene (i.e., cefE) was PCR cloned from *Streptomyces clavuligerus* and inserted into pET30a NdeI-Hind III site, and the resulted plasmid was designated as pYS16. The Quick Change Mutagenesis Kit was used to produce site-directed mutants of pYS16. The mutated sites were chosen based on the crystal structure of DAOCS (Valegard K. et al., *Nature*, 394:805–809 (1998)) using Swiss-Pdb Viewer (V3.7b2) program by selecting residuals surrounding active center within 10 Å. Each site was changed to Ala residual first, then a positive charge residual, a hydrophobic residual and a sulfur-containing residual. The primers were designed according to the manufacturer's manual. The resulted mutants were confirmed by DNA sequencing the harbored plasmids, and the cell crude extracts were prepared and subjected for DAOCS activity assay.

Example 4

DAOCS Activity Assays

BL21(DE3) transformants were grown overnight in 5 ml of LB medium with 50 μg/ml kanamycin at 30° C. This culture was used to inoculate 100 ml of the same medium and grown at 30° C. for 1 hour. Then 0.1 mM IPTG was added to induce DAOCS indirectly at 30° C. for 4 hours. Cells were harvested, washed with buffer A (50 mM Mops/pH 7.5, 1 mM PMSF, 1 mM DTT, and 0.5 μg/ml leupeptin), lysed by sonication (VCX 750; Sonics & Materials, USA), and centrifuged at 15,000×g for 15 minutes. The supernatant was used as a cell extract.

For penicillin G, 20 μl of cell extracts was added into a standard 200 μl assay reaction containing 50 mM Mops/pH 7.5, 4 mM ascorbate, 1 mM FeSO$_4$, 4 mM α-ketoglutarate and 7 mM penicillin G, and incubated at 30° C. for 20 minutes. The reaction was stopped by addition of 200 μl of ethanol, followed by a centrifugation at 15,000×g for 5 minutes. The concentration of cephalosporin G in supernatant was analyzed by HPLC with 40 μl injection. The mobile phase was 25 mM potassium phosphate/pH 6.5 with 19% acetonitrile at a flow rate of 1 ml/min. The retention time for cephalosporin G was 8.5 minutes and 12.5 minutes for penicillin G with detection at 215 nm, and the product at 8.5 minutes in DAOCS reaction was confirmed by LC-MS to have a molecular weight of 370. The site-directed mutants such as YS49 (L277K), YS8 (I305L), YS11 (I305M), and Y12 (N304K) having higher expandase activities on penicillin G than the parent strain YS16 were obtained. The different combinations of the mutated amino acids mentioned above were also constructed by site-directed mutagenesis.

Example 5

DAOCS Purification

Figure 2:
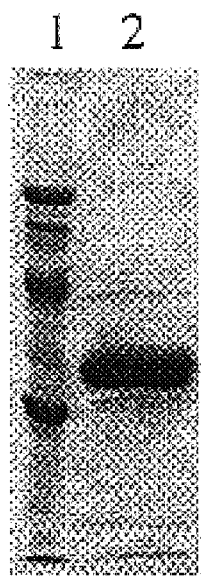
FIG. 2 shows the SDS-PAGE results of the purified DAOCS of the invention. Lanes 1 and 2 represent molecular weight markers and the purified DAOCS of YS67 mutant, respectively. The loaded DAOCS dose was in an amount of 5 μg.
Figure 3:
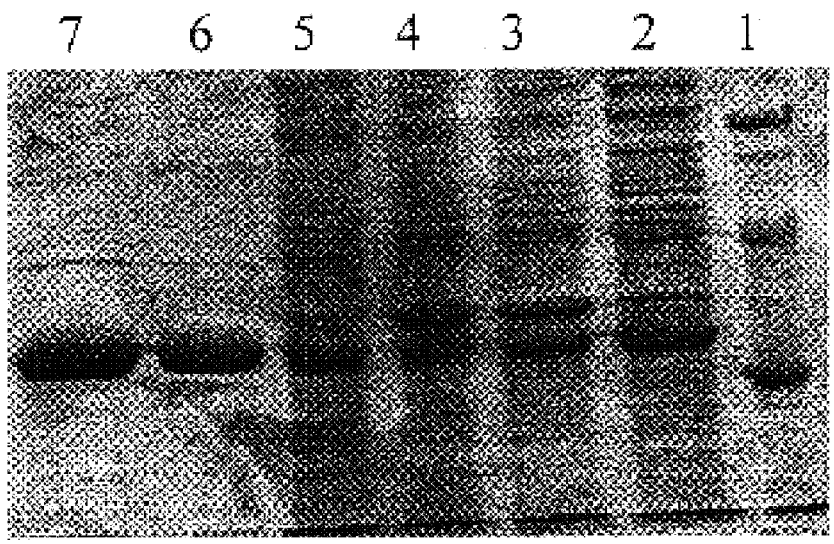
FIG. 3 shows the SDS-PAGE results of the purified DAOCS of the invention. Lanes 1 represents molecular weight markers. Lanes 2 to 5 represent samples irrelevant to the invention. Lanes 6 and 7 represent the purified DAOCS of SC29 and SC39 mutants, respectively. The loaded DAOCS dose was in an amount of 5 μg.
Figure 4:
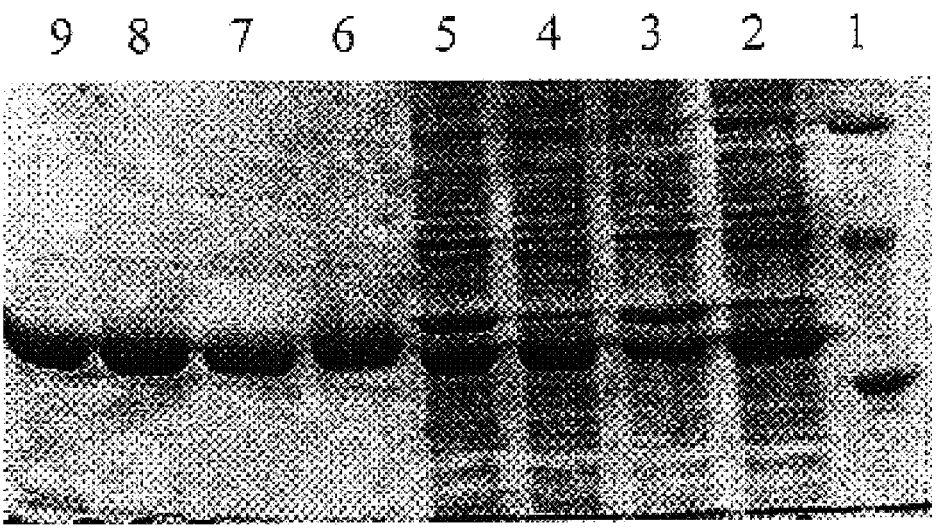
FIG. 4 shows the SDS-PAGE results of the purified DAOCS of the invention. Lanes 1 represents molecular weight markers. Lanes 2 to 5 represent samples irrelevant to the invention. Lanes 6 to 9 represent the purified DAOCS of YS98, YS108, YS115 and YS125, respectively. The loaded DAOCS dose was in an amount of 5 μg.

The cell extract (2 ml) of a candidate mutant was applied onto a HiTrap Q column (5 ml) equilibrated with buffer B (50 mM Mops/pH 7.5, 1 mM DTT, 0.4 mM pefabloc SC, and 0.5 μg/ml leupeptin). Then, the column was washed with 20 ml of buffer B, followed by a further wash with 25 ml of 120 mM NaCl in buffer B, and DAOCS was eluted off with 20 ml of 150 mM NaCl in buffer B. The DAOCS containing fractions were pooled (10 ml), concentrated by UF 15 device (NMWL 5K; Millipore), and loaded onto a Hiload Superdex 75 (16/60) column pre-equilibrated with buffer B at a flow rate at 1 ml/min. The DAOCS thus purified had a purity more than 90% as judged by SDS-PAGE, see FIGS. 1 and 2, and was stored in 1 mM DTT and 2 mg/ml BSA at −80° C. immediately.

Example 6

Kinetic Assays of Purified DAOCS

The standard penicillin G assay was followed for Kinetic assay, but 20 μg of purified DAOCS was used and the concentration of α-ketoglutarate was reduced to 1 mM. Kinetic parameters were obtained from triplicate experiments by Hanes-Woolf Plot. For assays using penicillin N as main substrate, a total volume of 240 μl reaction containing 50 mM Hepes/pH 7.5, 0.4 mM ascorbate, 0.1 mM FeSO$_4$, 0.1 mM α-ketoglutarate, 0.1 mM penicillin N and 0.5 μg of purified DAOCS was incubated at 30° C. for 10 minutes, then the same volume of 10 mM EDTA/pH 7.5 was added, and the mixture was subjected to ultrafiltration with UF 0.5 device (NMWL 5000, Millipore). The filtrate was analyzed by HPLC using 25 mM potassium phosphate/pH 6.5 as a mobile phase. The retention time of DAOC and penicillin N was 12 minutes and 13.5 minutes, respectively. The results of kinetic parameters are shown in Table 1, wherein the definition and calculation of the parameters are described in Lehninger et al. *Principles of Biochemistry*, 2.sup.nd Ed. Worth Publishers, New York (1993) which is incorporated herein for reference.

TABLE 1

Kinetic parameters for penicillin N and penicillin G

| Strains | Km (mM) | k$_{cat}$ (S$^{-1}$) | k$_{cat}$/Km (M$^{-1}$S$^{-1}$) |
|---|---|---|---|
| For penicillin N: | | | |
| YS16 (wild-type) | 0.014 ± 0.006 | 0.307 ± 0.038 | 22,000 |
| YS5(V275I) | 0.012 ± 0.003 | 0.252 ± 0.020 | 20,000 |
| YS8(I305L) | 0.006 ± 0.002 | 0.284 ± 0.030 | 44,000 |
| YS11(I305M) | 0.012 ± 0.001 | 0.310 ± 0.004 | 26,000 |
| YS12 (N304K) | 0.004 ± 0.001 | 0.366 ± 0.023 | 92,000 |
| YS125(N304L) | 0.018 ± 0.004 | 0.415 ± 0.063 | 23,000 |
| YS49(L277K) | 0.011 ± 0.005 | 0.220 ± 0.042 | 20,000 |
| YS53(C281Y) | 0.006 ± 0.001 | 0.273 ± 0.014 | 47,000 |
| YS59(G79E) | 0.009 ± 0.003 | 0.178 ± 0.019 | 20,000 |
| YS115(M73T) | 0.006 ± 0.003 | 0.239 ± 0.009 | 40,000 |
| YS67(V275I & I305M) | 0.013 ± 0.005 | 0.316 ± 0.032 | 24,000 |
| For penicillin G: | | | |
| YS16 (wild-type) | 2.58 ± 0.22 | 0.0302 ± 0.0007 | 12 |
| YS5(V275I) | 1.68 ± 0.20 | 0.0335 ± 0.0008 | 20 |
| YS8(I305L) | 0.66 ± 0.07 | 0.0506 ± 0.0010 | 77 |
| YS11(I305M) | 0.75 ± 0.04 | 0.0968 ± 0.0013 | 129 |
| YS12 (N304K) | 0.22 ± 0.03 | 0.0376 ± 0.0002 | 171 |
| YS125(N304L) | 0.55 ± 0.12 | 0.0268 ± 0.0004 | 49 |
| YS49(L277K) | 0.72 ± 0.02 | 0.0343 ± 0.0005 | 48 |
| YS53(C281Y) | 0.68 ± 0.34 | 0.0496 ± 0.0022 | 73 |
| YS59(G79E) | 0.75 ± 0.02 | 0.0210 ± 0.0002 | 28 |
| YS115(M73T) | 0.74 ± 0.16 | 0.0418 ± 0.0014 | 56 |
| YS67(V275I & I305M) | 0.25 ± 0.08 | 0.0972 ± 0.025 | 389 |

As shown in Table 1, all mutants have expansion activities 2 to 32 folds higher on penicillin G than wild-type expandase as implicated in k$_{cat}$/Km (M$^{-1}$S$^{-1}$) parameters. In contrast, these mutants do not cause significant changes in kinetic parameters obtained with penicillin N, except for mutant YS12 which has expansion activities 4 folds higher than wild-type YS16. Making a comparison between YS12 (N304K) of the invention and YS125 (N304L) as disclosed in Chih H. S. et al supra, YS125 has the expansion activity 4 folds higher on penicillin G than wild-type expandase, and YS12 has the expansion activity 14 folds higher on penicillin G than wild-type expandase.

The relative activities of the mutants are determined according to Chih H. S. et al supra with the activity of wild-type DAOCS as 100% and shown in Table 2. The assay was performed with 1 mM penicillin G, and the other conditions were the same as standard assay.

TABLE 2

The relative activities of purified combinated mutants compared to wild type DAOCS

| Strains | Mutated sites | Relative Activities (%) |
|---|---|---|
| YS16 | — | 100 |
| YS67 | 275I, 305M | 500 |
| YS74 | 275I, 304K, 305L | 300 |
| YS81 | 275I, 281Y, 305M | 1290 |
| YS88 | 79E, 275I, 281Y | 430 |

TABLE 2-continued

The relative activities of purified combinated mutants compared to wild type DAOCS

| Strains | Mutated sites | Relative Activities (%) |
|---|---|---|
| YS94 | 281Y, 304K, 305M | 650 |
| YS96 | 79E, 275I, 305M | 1110 |
| YS100 | 79E, 275I, 305L | 470 |
| YS76 | 79E, 275I, 281Y, 305L | 250 |
| YS108 | 300V | 410 |
| SC29 | 275I, 281Y, 300V | 620 |
| 8C39 | 73T, 281Y | 610 |

What is claimed is:

1. A mutated penicillin expandase, derived from a wild-type expandase of a Streptomyces species, wherein the mutated penicillin expandase has a substitution at one or more amino acid residues selected from the group consisting of residues corresponding to methionine 73, glycine 79, valine 275, leucine 277, cysteine 281, and glycine 300 of SEQ ID NO: 1.

2. The mutated penicillin expandase of claim 1, wherein the Streptomyces species is *Streptomyces clavuligerus*.

3. A mutated penicillin expandase of claim 1 wherein, the residue corresponding to methionine 73 is substituted by threonine, the residue corresponding to glycine 79 is substituted by glutamic acid, the residue corresponding to valine 275 is substituted by isoleucine, the residue corresponding to leucine 277 is substituted by lysine, the residue corresponding to cysteine 281 is substituted by tyrosine, and the residue corresponding to glycine 300 is substituted by valine.

4. A mutated penicillin expandase derived from the penicillin expandase of claim 1, wherein the mutated penicillin expandase has a further substitution at one or more amino acid residues selected from the group consisting of residues corresponding to asparagine 304 and isoleucine 305 of SEQ ID NO: 1.

5. The mutated penicillin expandase of claim 4, wherein the residue corresponding to asparagine 304 is substituted by lysine and the residue corresponding to isoleucine 305 is substituted by leucine or methionine.

6. The mutated penicillin expandase of claim 3, wherein the mutated penicillin expandase has a further substitution at one or more amino acid residues selected from the group consisting of residues corresponding to asparagine 304 and isoleucine 305 of SEQ ID NO: 1 and wherein the residue corresponding to asparagine 304 is substituted by lysine and the residue corresponding to isoleucine 305 is substituted by leucine or methionine.

* * * * *